United States Patent [19]

Wehinger et al.

[11] Patent Number: 4,675,329

[45] Date of Patent: Jun. 23, 1987

[54] ISOPROPYL 2-(3-TRIFLUOROMETHYLPHENOXY)-ETHYL 1,4-DIHYDRO-2,6-DIMETHYL-4-(3-NITROPHENYL)-PYRIDINE-3,5-DICARBOXYLATE AS VASO-DILATORS

[75] Inventors: Egbert Wehinger; Andreas Knorr; Kurt Stoepel, all of Wuppertal; Arend Heise, Aurich, all of Fed. Rep. of Germany

[73] Assignee: Bayer Aktiengesellschaft, Leverkusen, Fed. Rep. of Germany

[21] Appl. No.: 750,561

[22] Filed: Jun. 27, 1985

[30] Foreign Application Priority Data

Jul. 3, 1984 [DE] Fed. Rep. of Germany ....... 3424342

[51] Int. Cl.[4] .................. C07D 211/90; A61K 31/455
[52] U.S. Cl. ..................................... 514/356; 546/321
[58] Field of Search ........................ 546/321; 514/356

[56] References Cited

U.S. PATENT DOCUMENTS 4,044,141  8/1977  Bossert et al. ...................... 546/321

Primary Examiner—Henry R. Jiles
Assistant Examiner—Dale A. Bjorkman
Attorney, Agent, or Firm—Sprung Horn Kramer & Woods

[57] ABSTRACT

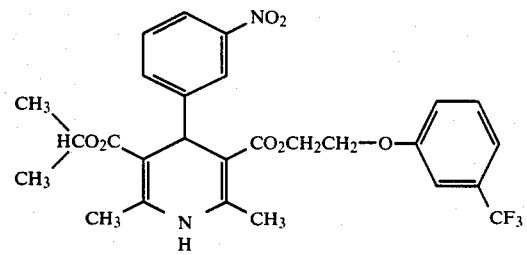

is a vaso-dilator effective in combating hypertension and circulatory disorders.

4 Claims, No Drawings

ISOPROPYL 2-(3-TRIFLUOROMETHYLPHENOXY)-ETHYL 1,4-DIHYDRO-2,6-DIMETHYL-4-(3-NITROPHENYL)-PYRIDINE-3,5-DICARBOXYLATE AS VASO-DILATORS

The present invention relates to isopropyl 2-(3-trifluoromethylphenoxy)-ethyl 1,4-dihydro-2,6-dimethyl-4-(3-nitrophenyl)-pyridine-3,5-dicarboxylate, several processes for its preparation and its use in medicaments.

It is known that certain 1,4-dihydropyridines have interesting pharmacological properties (F. Bossert and W. Vater, Naturwissenschaften, 58, 578 (1971)).

It has now been found that isopropyl 2-(3-trifluoromethylphenoxy)-ethyl 1,4-dihydro-2,6-dimethyl-4-(3-nitrophenyl)-pyridine-3,5-dicarboxylate of the formula I

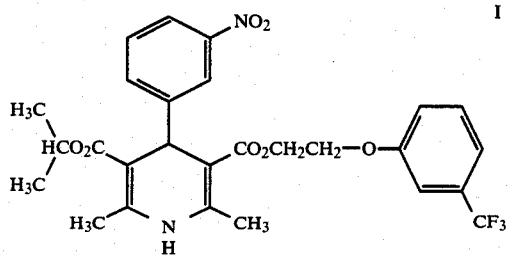

has a preferential long-lasting periphero-vasodilating action and can thus be employed as an active compound in medicaments.

It has furthermore been found that the new active compound of the formula I is obtained by a process in which (A) isopropyl 2-(3-nitrobenzylidene)-acetoacetate of the formula II

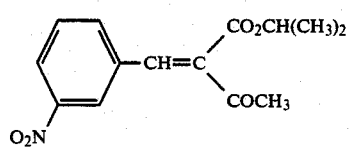

is reacted with 2-(3-trifluoromethylphenoxy)-ethyl 3-aminocrotonate of the formula III

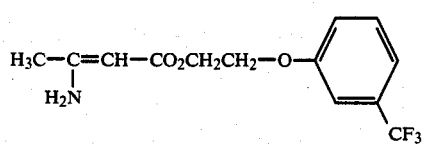

as such or in the presence of water and/or inert organic solvents, or (B) isopropyl 2-(3-nitrobenzylidene)-acetoacetate of the formula II is reacted with 2-(3-trifluoromethylphenoxy)-ethyl acetoacetate of the formula IV

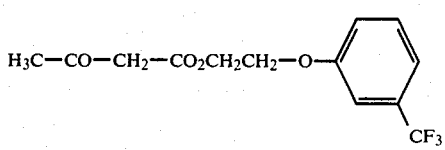

and ammonia, as such or in the presence of water and/or inert organic solvents, or (C) 2-(3-trifluoromethylphenoxy)-ethyl 2-(3-nitrobenzylidene)-acetoacetate of the formula V

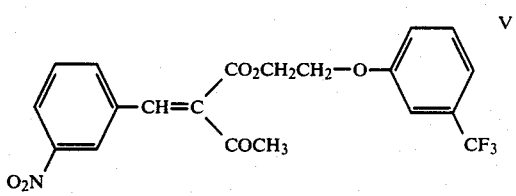

is reacted with isopropyl-3-aminocrotonate of the formula VI

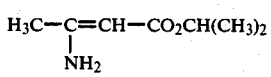

as such or in the presence of water and/or inert organic solvents, or (D) 2-(3-trifluoromethylphenoxy)-ethyl 2-(3-nitrobenzylidene)-acetoacetate of the formula V is reacted with isopropyl acetoacetate of the formula VII

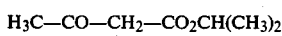

and ammonia, as such or in the presence of water and/or inert organic solvents, or (E) 3-nitrobenzaldehyde of the formula VIII

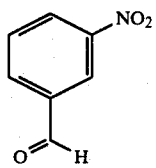

is reacted with 2-(3-trifluoromethylphenoxy)-ethyl acetoacetate of the formula IV and isopropyl 3-aminocrotonate of the formula VI, as such or in the presence of water and/or inert organic solvents, or (F) 3-nitrobenzaldehyde of the formula VIII is reacted with 2-(3-trifluoromethylphenoxy)-ethyl 3-aminocrotonate of the formula III and isopropyl acetoacetate of the formula VII, as such or in the presence of water and/or inert organic solvents.

Surprisingly, the substance according to the invention, of the formula I, has a preferential long-lasting periphero-vasodilating action.

Such a preferential long-lasting peripheral vasodilation has not hitherto been found in the series of similar 1,4-dihydropyridine derivatives known from the prior art, so that the compound according to the invention represents an enrichment of pharmacy in respect of this particular property.

The compound according to the invention is chiral and can exist in stereoisomeric forms which behave as mirror images (enantiomers, antipodes). These can in turn again appear in various conformations. The present invention relates to both the racemic form and the antipodes.
Depending on the nature of the starting substances used, the synthesis of the compound according to the invention can be represented by the following equations:
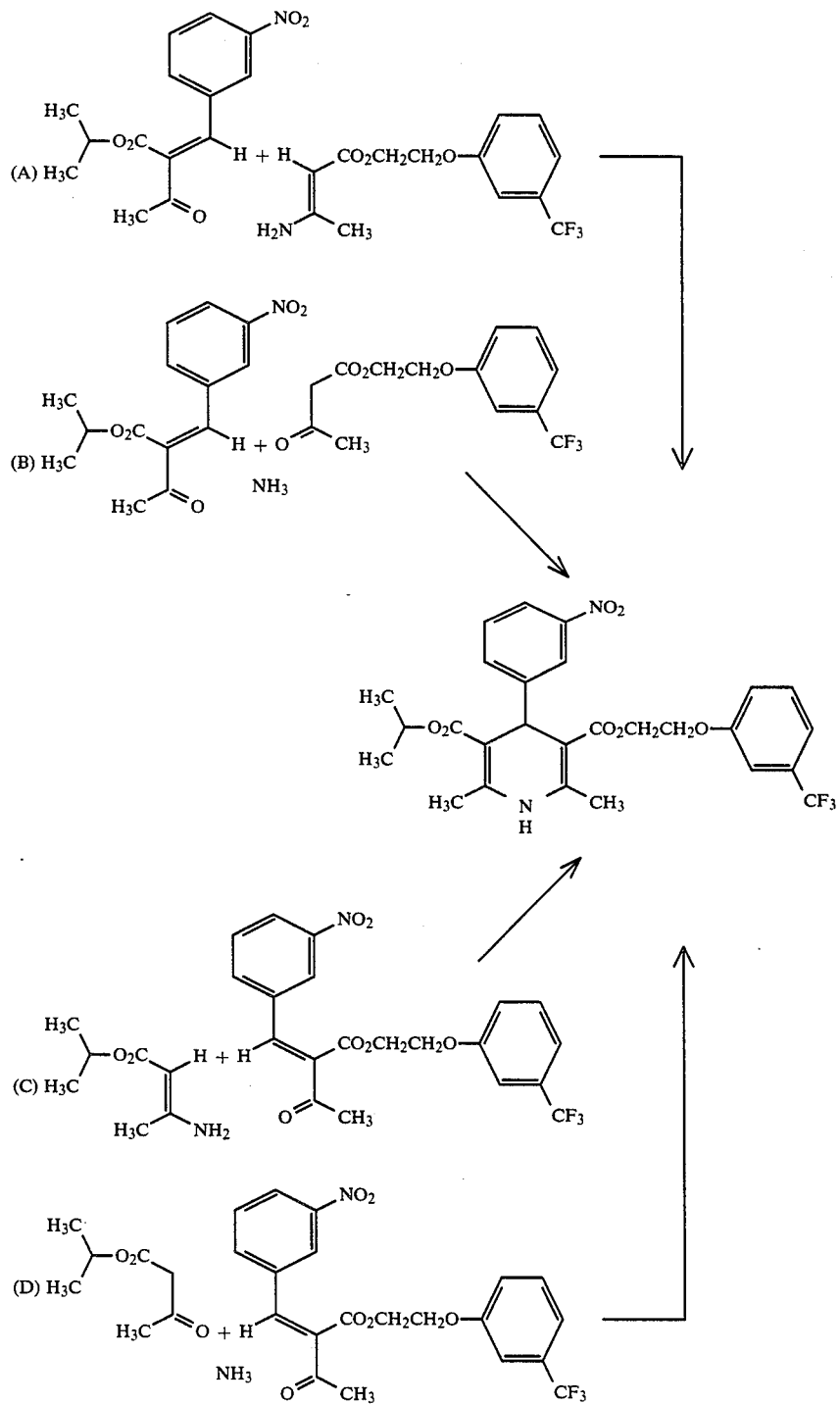

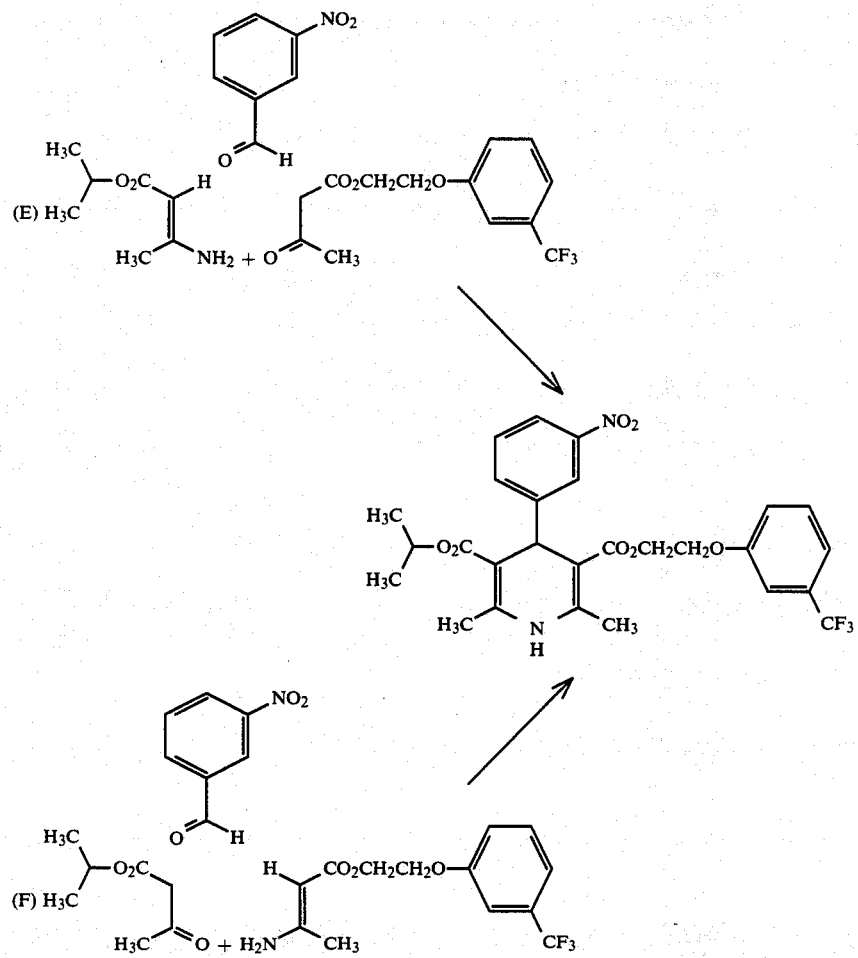

The substances of the formulae II to VIII used as starting materials are known from the literature or can be prepared by methods which are known from the literature (see, for example, G. Jones "The Knoevenagel Condensation" in Org. Reactions, Volume XV, 204 et seq. (1967); A. C. Cope, J. Amer. Chem. Soc. 67, 1017 (1945); and D. Borrmann, "Umsetzung von Diketen mit Alkoholen, Phenolen und Mercaptanen" ("Reaction of diketene with alcohols, phenols and mercapstans") in Houben-Weyl, Methoden der Organischen Chemie (Methods of Organic Chemistry), Volume VII/4, 230 et seq. (1968)).

In carrying out processes A–F according to the invention, the substances participating in the reaction are in each case employed in approximately equimolar amounts. The ammonia used is advantageously added in excess, and in particular preferably in amounts of 1.5–2.5 moles in each case per mole of another starting substance.

Possible solvents are water and all the inert organic solvents. These include, preferably, alcohols, such as ethanol, methanol or propanol, or ethers, such as diethyl ether, tetrahydrofuran or dioxane, or glacial acetic acid, pyridine, dimethylformamide, dimethylsulphoxide, acetonitrile or hexamethylphosphoric acid triamide.

The reaction temperatures can be varied within a substantial range. In general, the reaction is carried out between 20° C. and 200° C., preferably at 50° C. to 120° C. or, in particular, at the boiling point of the particular solvent.

The reaction can be carried out under normal pressure, but also under increased pressure. In general, the reaction is carried out under normal pressure.

The above preparation processes are given merely for illustration and the preparation of the compound I is not restricted to these processes, but any modification of these processes can be applied in the same manner to the preparation of the compound I.

Preparation processes A and C according to the invention may be mentioned as preferred.

The compound according to the invention is a substance which can be used as a medicament. On enteral and parenteral administration, it effects strong and long-lasting peripheral vasodilation and can thus be employed for the therapy and prophylaxis of the hypertension and/or peripheral circulatory disturbances. The compound can thus be used for combating diseases.

The new active compound can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present here in a concentration of about 0.5 to 90 percent by weight of the total mixture, that is to say in amounts which suffice to achieve the dosage range mentioned.

The formulations are prepared, for example, by extending the active compound with solvents and/or excipients, if appropriate using emulsifiers and/or dispersing agents, and, for example when using water as the diluent, organic solvents can be used as auxiliary solvents, if appropriate.

Examples of auxiliaries which may be mentioned are: water, non-toxic organic solvents, such as paraffins (for example petroleum fractions), vegetable oils (for example groundnut-sesame oil), alcohols (for example ethyl alcohol and glycerol) and glycols (for example propylene glycol and polyethylene glycol); solid excipients, such as, for example, natural rock powders (for example kaolins, aluminas, talc and chalk), synthetic rock powders (for example highly disperse silica and silicates) and sugars (for example sucrose, lactose and glucose); emulsifiers, such as non-ionic and anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

The formulations are administered in the customary manner, preferably enterally or parenterally, in particular orally or intravenously.

In the case of enteral administration, tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc can be co-used when making tablets. In the case of aqueous suspensions and/or elixirs which are intended for oral use, the active compounds can be mixed with various flavor-improving agents or colorants, in addition to the abovementioned auxiliaries.

In the case of parenteral use, solutions of the active compound can be employed, using suitable liquid excipients.

In general, it has proved advantageous, in the case of intravenous administration, to administer amounts of about 0.0001 to 1 mg/kg, preferably about 0.0014 to 0.10 mg/kg of body weight per day to achieve effective results, and in the case of enteral administration the dosage is about 0.01 to 10 mg/kg, preferably 0.1 to 1.0 mg/kg of body weight per day.

Nevertheless, it can at times be necessary to deviate from the amounts mentioned, and in particular to do as a function of the body weight of the experimental animal or the nature of the administration route, but also because of the species of the animal and its individual behavior towards the medicament or the interval at which administration takes place.

Thus, in some cases it can suffice to manage with less than the abovementioned minimum amount, while in other cases the upper limit mentioned must be exceeded. In the case of administration of relatively large amounts, it may be advisable to distribute these into several individual administrations over the day.

The same dosage range is envisaged for administration in human medicine. The general sense of the above statements also applies here.

PREPARATION EXAMPLES

Isopropyl 2-(3-trifluoromethylphenoxy)-ethyl 1,4-dihydro-2,6-dimethyl-4-(3-nitrophenyl)-pyridine-3,5-dicarboxylate

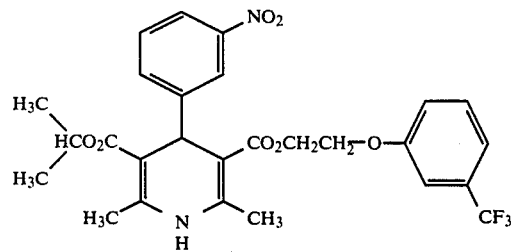

(A) A solution of 27.7 g (0.1 mole) of isopropyl 2-(3-nitrobenzylidene)-acetoacetate and 28.9 g (0.1 mole) of 2-(3-trifluoromethylphenoxy)-ethyl 3-aminocrotonate in 150 ml of ethanol was heated at the boiling point under nitrogen for 20 hours. The solvent was then distilled off in vacuo and the oily residue was made to crystallize by trituration with a little ether. The crude product was filtered off with suction and recrystallized from ethanol.

Melting point: 128°–130° C. Yield: 35 g (64%).

(B) 27.7 g (0.1 mole) of isopropyl 2-(3-nitrobenzylidene)-acetoacetate were heated under reflux together with 29 g (0.1 mole) of 2-(3-trifluoromethylphenoxy)-ethyl acetoacetate and 12 g (0.18 mole) of a 25% strength aqueous ammonia solution in 160 ml of isopropanol in a nitrogen atmosphere for 24 hours. The solvent was then distilled off in vacuo and the oily residue was made to crystallize. The crude product was filtered off with suction and recrystallized from ethanol.

Melting point: 128°–130° C. Yield: 26 g (47%).

(C) 42.3 g (0.1 mole) of 2-(3-trifluoromethylphenoxy)-ethyl 2-(3-nitrobenzylidene)-acetoacetate were heated under reflux together with 14.3 g (0.1 mole) of isopropyl 3-aminocrotonate in 150 ml of ethanol under nitrogen for 20 hours. The solvent was then distilled off in vacuo and the oily residue was thoroughly mixed with a little ether. After a short time, crystallization occurred. The crude product was filtered off with suction and recrystallized from ethanol.

Melting point: 128°–130° C. Yield: 31 g (57%).

(D) 42.3 g (0.1 mole) of 2-(3-trifluoromethylphenoxy)-ethyl 2-(3-nitrobenzylidene)-acetoacetate were heated under reflux together with 14.4 g (0.1 mole) of isopropyl acetoacetate and 12 g (0.18 mole) of a 25% strength aqueous ammonia solution in 150 ml of isopropanol in a nitrogen atmosphere for 24 hours. After the reaction mixture had cooled, the solvent was distilled off in vacuo and the oily residue was taken up in methylene chloride. The organic phase was washed with water and, after drying over anhydrous sodium sulphate, was concentrated in vacuo. The resulting oil was made to crystallize and the crude product was filtered off with suction and recrystallised from ethanol.

Melting point: 128°–130° C. Yield: 28 g (51%).

(E) A solution of 15.1 g (0.1 mole) of 3-nitrobenzaldehyde, 29 g (0.1 mole) of 2-(3-trifluoromethylphenoxy)-ethyl acetoacetate and 14.3 g of (0.1 mole) of isopropyl 3-aminocrotonate in 150 ml of dioxane was heated at the boiling point under nitrogen for 24 hours. The solvent was then distilled off in vacuo and the oily residue was made to crystallize by trituration with a little ether. The solid was filtered off with suction and recrystallized from ethanol.

Melting point: 128°–130° C. Yield: 25 g (46%).

(F) A solution of 15.1 g (0.1 mole) of 3-nitrobenzaldehyde, 28.9 g (0.1 mole) of 2-(3-trifluoromethylphenoxy)-ethyl 3-aminocrotonate and 14.4 g (0.1 mole) of isopropyl acetoacetate in 150 ml of isopropanol was heated to boiling under nitrogen for 24 hours. After the reaction mixture had cooled, the solvent was distilled off in vacuo, the residue was triturated with ether and the crystallized product was filtered off with suction and recrystallized from ethanol.

Melting point: 128°–130° C. Yield: 24 g (44%).

It will be understood that the specification and examples are illustrative but not limitative of the present invention and that other embodiments within the spirit and scope of the invention will suggest themselves to those skilled in the art.

What is claimed is:

1. Isopropyl 2-(3-trifluoromethylphenoxy)-ethyl 1,4-dihydro-2,6-dimethyl-4-(3-nitrophenyl)-pyridine-3,5-dicarboxylate of the formula

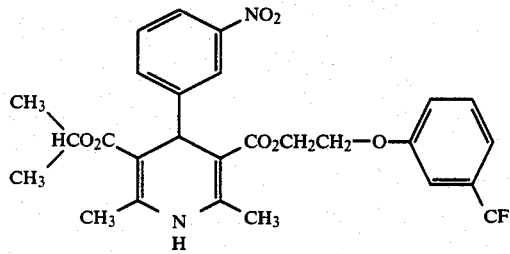

2. A vaso-dilating composition comprising a vaso-dilating effective amount of isopropyl 2-(3-trifluoromethylphenoxy)-ethyl 1,4-dihydro-2,6-dimethyl-4-(3-nitrophenyl)-pyridine-3,5-dicarboxylate of the formula

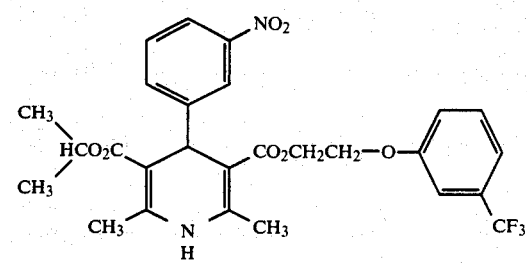

and a diluent.

3. A unit dose of a composition according to claim 2 in the form of a tablet, capsule or ampule.

4. A method of combating hypertension in a patient which comprises administering to such patient a vaso-dilating effective amount of isopropyl 2-(3-trifluoromethylphenoxy)-ethyl 1,4-dihydro-2,6-dimethyl-4-(3-nitrophenyl)-pyridine-3,5-dicarboxylate of the formula

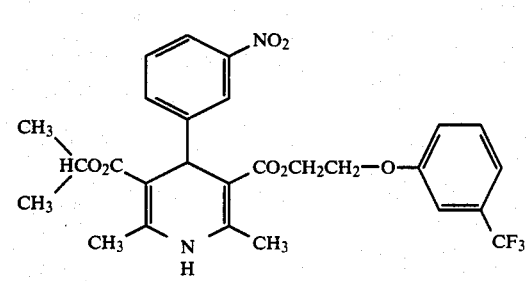

* * * * *